United States Patent
Greif et al.

(10) Patent No.: US 6,753,298 B2
(45) Date of Patent: Jun. 22, 2004

(54) AGENTS FOR COMBATING NEOSPORA SPEC

(75) Inventors: Gisela Greif, Remagen (DE); Folker Lieb, Leverkusen (DE); Carl Fedtke, Köln (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 10/307,721

(22) Filed: Dec. 2, 2002

(65) Prior Publication Data

US 2003/0100481 A1 May 29, 2003

Related U.S. Application Data

(63) Continuation of application No. 09/555,560, filed as application No. PCT/EP98/07460 on Nov. 20, 1998, now abandoned.

(30) Foreign Application Priority Data

Dec. 3, 1997 (DE) .......................................... 197 53 504

(51) Int. Cl.$^7$ .......................... A01N 47/10; A01N 33/18

(52) U.S. Cl. ...................... 504/300; 504/304; 504/347; 514/155; 514/478; 514/485; 514/646

(58) Field of Search ................................ 504/300, 304, 504/347; 514/155, 478, 485, 646

(56) References Cited

U.S. PATENT DOCUMENTS 3,111,403 A * 11/1963 Soper ........................... 71/2.3
5,877,186 A * 3/1999 Leef et al. ................... 514/315

OTHER PUBLICATIONS

Chan et al. "Plant Microtubule Inhibitors Against Trypanosomatids". Parasitology Today. 10(11):448–451. 1994.*
Devine et al. "Microtubule Disruptors", Chapter 10 in Physiology of Herbicide Action. NJ:PTR Prentice Hall. P. 189–224. 1993.*

* cited by examiner

Primary Examiner—S. Mark Clardy

(57) ABSTRACT

Compositions for controlling diseases caused by protozoans of the genus Neospora, which are characterized in that they comprise one or more active compounds which inhibit the microtubulin system of plants.

1 Claim, No Drawings

AGENTS FOR COMBATING NEOSPORA SPEC

The present invention relates to compositions for controlling diseases caused by parasites of the genus Neospora. The compositions according to the invention are based on inhibitors of the microtubulin system of plants.

Neosporosis is a disease of animals cause by parasites of the genus Neopspora, in particular *Neospora caninum*. Neospora infections are known in dogs, cattle, sheep, goats and horses.

The final host of Neospora spec such as *N. caninum*, and thus the complete life-history of the parasite, are as yet unknown. What is known as yet about the life-history of this parasite are only the asexual reproductive stages in the form of schizogony and the single-celled tachyzoites/bradyzoites. Tachyzoites are single-celled infectious parasitic stages with a size of 3-7×1–5 μm, which are formed in cysts in the tissue following intracellular multiplication. This reproductive process is termed endodyogeny.

The reproduction by tachyzoites preferentially takes place in organelles such as muscles and nerve cells. This is why the pathological symptoms following natural infection occur preferentially in these tissues. In dogs, for example, natural infection from week 5 to 6 leads to disease symptoms with signs of hypersensitivity due to inflammations of the nerve roots and increasing paresis of the hind legs. Further histopathological findings occur in the nerve system, preferentially in the brain and spinal cord. Extensive non-suppurative inflammations, glial proliferations and perivascular infiltrations with mononuclear cells (macrophages, lymphocytes, few plasma cells), in some cases also eosinophiles and neutrophiles, dominate here. Necrotic-degenerative changes occur in the muscular system and are even macroscopically visible. What is notable are long pale longitudinal stripes, in addition to a more or less pronounced atrophy.

In California and Australia, *Neospora caninum* infections are considered a main cause for abortion in herds of cattle.

In cattle, the disease symptoms are similar to those found in dogs. Ataxias occur, the articular reflexes are greatly reduced, and pareses occur on the hind legs, in some cases on all four legs. The histological symptoms are similar to those found in dogs: non-suppurative meningitis and myelitis predominate.

Only a very limited amount of information is available as yet on the in-vivo efficacy of substances suitable for controlling Neosporosis since adequate in-vivo test systems have yet to be developed. In experimentally infected mice, sulphadiazine (administered by drinking water) proved to be effective only when the treatment was prophylactic, i.e. before the onset of the infection. In dogs, the treatment with sulphadiazine and clindamycin is only successful when it starts very early at the first sign of clinical symptoms due to inflammation of the nerve roots.

The present invention relates to compositions for controlling diseases caused by protozoans of the genus Neospora, which are characterized in that they comprise one or more active compounds which inhibit the microtubulin system of plants.

Microtubuli (MT) belong to an important filament type of the cytoskeleton. The main component of this structure is tubulin, a globular polypeptide with a molar mass of 50,000 Daltons. During the intracellular aggregation of the microtubuli, subunits (heterodimers) composed of $\alpha$- and $\beta$-tubulin associate to first form protofilaments, which then give rise to a microtubulin tube of approximately 25 nm.

In biological organisms, MT have important functions with regard to cell shape and cell movement. In particular, MT are involved in maintaining cell polarity. Together with associated proteins (MaPs), MT are responsible, in a stable and permanent arrangement, for the gliding mechanism in cilia, a biological structure which specializes in causing repetitive movements.

Polymerization (synthesis) and depolymerization (degradation) are based on an exchange of tubulin molecules between the MT and a stock which is dissolved in the cytoplasma. The sensitive balance of synthesis and degradation within a cell can be disturbed by substances which increase, or inhibit, polymerization. This process can be blocked by tubulin-binding substances, the so-called MT inhibitors. MT inhibitors are a group of structurally diverse compounds which can be produced by fungi, plants or marine organisms or synthesized in the laboratory. Colchicine, an alkaloid obtained from the autumn crocus, binds firmly to tubulin and thus prevents polymerization. Other inhibitors which have been known for a long time are vinblastin, vincristin and taxol. Taxol stabilizes the MT structures and prevents their degradation (Wilson L (1975) Life Sci. 17: 303–310). Benzimidazoles (BZ) are an example of a class of compound with therapeutic activity against helminths (Horton RJ (1990) Parasitology Today 6(4): 106; Townsend LB and Wise DS (1990) Parasitology Today 6(4): 107–112). BZ are synthetic inhibitors of in-vitro polymerization of mammalian tubulin, which show a higher in-vivo affinity for helminth tubulin than for the mammalian cell (Lacey E (1988) Int. J. Parasitol. 18, 885–936). Competitive ligands binding studies on H3-colchicine confirm that BZ interact with the colchicin-binding domain and thus prevent polymerization (Friedman Pa. and Platzer EG (1978) Biochim. Acta 544, 605–614).

In plant cells, the MT system participates especially in generating cell shape and cell polarity and also governs chromosomal distribution during mitosis. Herbicides which act on the MT system thus interrupt the cell cycle (Hess FD (1987) Rev. Weed Sci 3: 183–203). The morphological consequence of the herbicidal action are giant cells with giant nuclei, polynucleate cells, tissue swellings and eventually growth is halted permanently.

Even though the sequence of tubulin from various species shows a high degree of homology, drastic differences exist in some cases between plant and animal tubulin. Thus, for example, animal tubulin polymerizes spontaneously in vitro, while this is not the case with plant tubulin. This means that it is not possible from the outset to extrapolate, to animal tubilin, findings which have been obtained with and on plant tubulin, and vice versa.

Active compounds which can be used in accordance with the invention are compounds which inhibit the microtubulin system of plants. These preferably include herbicidal compounds of the classes of the 2,6-dinitroanilines and the N-arylcarbamates.

Especially preferred are 2,6-dinitroanilines of the following formula (I)

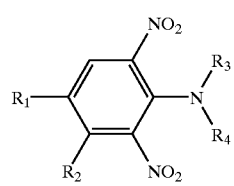

in which
R$_1$ represents hydrogen, halogen, nitro, cyano, alkyl, alkenyl, alkoxy, alkenyloxy, alkylthio, alkylsulphinyl, alkylsulphonyl, halogenoalkyl, halogenoalkenyl, halogenoalkoxy, halogenoalkenyloxy, aminosulphonyl, alkylsulphonylamino,
R$_2$ represents hydrogen, halogen, amino, alkyl, alkoxy,
R$_3$ represents hydrogen, alkyl, alkenyl, alkinyl, cycloalkyl-alkyl, alkyloxy, halogenoalkyl,
R$_4$ represents alkyl, alkenyl, alkinyl, cycloalkyl-alkyl, alkyloxy, halogenoalkyl,
R$_3$ and R$_4$ together with the nitrogen to which they are bonded form a heterocyclic radical.

Especially preferred are the N-arylcarbamates of the formula (II)

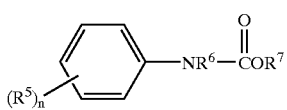

in which
R$^5$ represents hydrogen, halogen,
R$^6$ represents hydrogen, alkyl, alkenyl,
R$^7$ represents alkyl, alkenyl, alkinyl, halogenoalkyl, halogenoalkenyl, halogenoalkinyl,
n represents 1 or 2.

Optionally substituted alkyl alone or as a constituent of one of the radicals alkoxy, alkylthio, alkylsulphinyl, alkylsulphonyl, halogenoalkyl, cycloalkylalkyl in the general formulae denotes straight-chain or branched alkyl having preferably 1 to 6, in particular 1 to 4, carbon atoms. Examples which may be mentioned are optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl, Methyl, ethyl, n-propyl, isopropyl, n-butyl, isobutyl, sec-butyl and tert-butyl may be mentioned as being preferred.

Optionally substituted alkenyl alone or as a constituent of one of the radicals alkeneoxy, halogenoalkenyl, halogenoalkenyloxy in the general formulae denotes straight-chain or branched alkenyl having preferably 1 to 6, in particular 1 to 4, carbon atoms. Examples which may be mentioned are optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-pro-penyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-prope-nyl, 1-ethyl-1-methyl-2-propenyl and 1-ethyl-2-methyl-2-propenyl. Optionally substituted ethenyl, 2-propenyl, 2-butenyl or 1-methyl-2-propenyl may be mentioned as being preferred.

Optionally substituted cycloalkyl alone or as a constituent of one of the radicals cycloalkylalkyl in the general formulae denotes mono-, bi- and tricyclic cycloalkyl, preferably having 3 to 10, in particular 3, 5 or 7, carbon atoms. Examples which may be mentioned are optionally substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Optionally substituted alkinyl and the alkinyl moiety of halogenoalkinyl in the general formulae denote straight-chain or branched alkinyl having preferably 2 to 6, in particular 2 to 4, carbon atoms. Optionally substituted ethinyl, prop-1-inyl, prop-2-inyl and but-3-inyl may be mentioned by way of example and as being preferred.

Halogen substituents of the radicals halogenoalkyl, halogenoalkenyl, halogenoalkinyl, halogenoalkoxy, halogenoalkenyloxy, which may be mentioned as being preferred are fluorine, chlorine, bromine, in particular fluorine or bromine.

The following halogen-substituted radicals may be mentioned individually: trifluoromethyl, chlorodifluoromethyl, difluoromethyl, trichloromethyl, pentafluoroethyl, chlorofluoro-ethyl, trifluoromethoxy, perfluoroethylene, perfluoroethyleneoxy, chloropropinyl, fluoropropinyl.

The abovementioned 2,4-dinitroanilines and N-arylcarbamates are known compounds or can be prepared in a simple manner by known methods.

The 2,4-dinitroanilines include the following active compounds with the common names trifluralin, benfluralin, profluralin, dinitramine, nitralin, oryzalin, isopropalin, ethalfluralin, dipropalin, and derivatives and homologues of these compounds.

The N-arylcarbamates include the following active compounds with the common names propham (IPC), chlorpropham (CIPC), barbane, chlorbufam, swep, and derivatives and homologues of these compounds.

The active compounds are suitable for controlling parasites of the genus Neospora, which occur in animal keeping and animal breeding in livestock, breeding animals, zoo animals, laboratory animals, experimental animals and pets while having favourable toxicity to warm-blooded species. They are effective against all or individual developmental stages of the pests and against resistant and normally sensitive species.

The livestock and breeding animals include mammals such as, for example, cattle, horses, sheep, pigs, goats, camels, water buffalo, donkeys, rabbits, fallow deer, reindeer, fur-bearers such as, for example, mink, chinchilla, racoons, birds such as, for example, chickens, geese, turkeys, ducks.

Laboratory and experimental animals include, mice, rice, guinea pigs, golden hamsters, dogs and cats.

Pets include dogs and cats.

Administration may be both prophylactic and therapeutic.

The active compounds are administered enterally, parenterally, dermally or nasally, directly or in the form of suitable preparations.

The active compounds are administered enterally for example orally in the form of powders, suppositories, tablets, capsules, pastes, drinks, granules, drenches, boluses, medicated feed or drinking water. Dermal administration is effected, for example, in the form of dipping, spraying, bathing, washing, pouring-on and spotting-on and dusting. Parental administration is effected for example, in the form of an injection (intramuscular, subcutaneous, intravenous, intraperitoneal), or by implants.

Suitable preparations are:

Solutions such as solutions for injection, oral solutions, concentrates for oral administration after dilution, solutions for use on the skin or in body cavities, pour-on and spot-on formulations, gels;

Emulsions and suspensions for oral or dermal administration, and for injection; semi-solid preparations;

Formulations in which the active compound is incorporated in an ointment base or in an oil-in-water or water-in-oil emulsion base;

Solid preparations such as powders, premixes or concentrates, granules, pellets, tablets, boluses, capsules; aerosols and inhalants, active-compound-containing shaped articles.

Solutions for injection are administered intravenously, intramuscularly and subcutaneously.

Solutions for injection are prepared by dissolving the active compound in a suitable solvent, and, if appropriate, adding additives such as solubilizers, acids, bases, buffer salts, antioxidants, preservatives. The solutions are filter-sterilized and packaged.

The following may be mentioned as solvents: physiologically acceptable solvents such as water, alcohols such as ethanol, butanol, benzyl alcohol, glycerin, hydrocarbons, propylene glycol, polyethylene glycols, N-methylpyrrolidone and mixtures of these.

If appropriate, the active compounds can also be dissolved in physiologically acceptable vegetable or synthetic oils which are suitable for injection.

The following may be mentioned as solubilizers: solvents which promote the solution of the active compound in the main solvent or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the use concentration. Oral solutions and concentrates are prepared as described above for the injection solutions, but sterile procedures can be dispensed with.

Solutions for use on the skin are applied dropwise, smoothed on, rubbed in, splashed on, sprayed on or applied by immersion (dipping, bathing or washing). These solutions are prepared as described above in the solutions for injection.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and methacrylates.

Gels are applied to or smoothed onto the skin or introduced into body cavities. Gels are prepared by treating solutions which have been prepared as described for the solutions for injection with such an amount of thickener that a clear composition with an ointment-like consistency results. Thickeners used are those indicated further above.

Pour-on and spot-on formulations are poured, spotted or sprayed onto limited areas of the skin, the active compound either penetrating the skin and acting systemically, or distributing itself over the body surface.

Pour-on and spot-on formulations are prepared by dissolving, suspending or emulsifying the active compound in suitable solvents or solvent mixtures which are dermatologically acceptable. If appropriate, other adjuvants such as colorants, absorption accelerators, antioxidants, UV stabilizers or tackifiers are added.

Solvents which may be mentioned are: water, alkanols, glycols, polyethylene glycols, polypropylene glycols, glycerin, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2-dimethyl-4-oxy-methylene-1,3-dioxolane.

Colorants are all colorants which are licensed for use on animals and which can be dissolved or suspended.

Absorption accelerators are, for example, DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphate, ascorbic acid, butylhydroxytoluene, butylhydroxyanisole, tocopherol.

UV stabilizers are, for example, materials of the class of benzophenones or novantisolic acid.

Tackifiers are, for example, cellulose derivatives, starch derivatives, polyacrylates, natural polymers such as alginates, gelatine.

Emulsions can be administered orally, dermally or as an injection.

Emulsions are either of the water-in-oil type or of the oil-in-water type.

They are prepared by dissolving the active compound either in the hydrophobic or in the hydrophilic phase and halogenizing this phase with the solvent of the other phase with the aid of suitable emulsifiers and, if appropriate, further adjuvants such as colorants, absorption accelerators, preservatives, antioxidants, UV stabilizers, thickeners.

The following may be mentioned as hydrophobic phase (oils): liquid paraffins, silicone oils, natural vegetable oils such as sesame seed oil, almond oil, castor oil, synthetic triglycides such as caprylic/capric biglyceride, triglyceride mixture with vegetable fatty acid of chain length $C_8$–$C_{12}$ or other specifically selected natural fatty acids, partial glyceride mixtures of saturated or unsaturated, optionally also hydroxyl-group-containing fatty acids, mono- and diglycerides of the $C_8$/$C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as synthetic duck ureopygial fat, dibutyl phthalate, diisopropyl adipate, ester mixtures related to the latter and the like.

Fatty alcohols such as isotridecyl alcohol, 2-octyldodecanol, cetyl stearyl alcohol, oleyl alcohol.

Fatty acids such as, for example, oleic acid and its mixtures.

The following may be mentioned as hydrophilic phase: water, alcohols such as, for example, propylene glycol, glycerin, sorbitol and their mixtures.

The following may be mentioned as emulsifiers:

nonionic surfactants, for example polyoxyethylated castor oil, polyoxyethylated sorbitan monooleate, sorbitan monostearate, glycerin monostearate, polyoxyethyl stearate, alkylphenol polyglycol ether;

ampholytic surfactants such as disodium N-lauryl-β-iminodipropionate or lecithin;

anionic surfactants such as sodium lauryl sulphate, fatty alcohol ether sulphates, mono/dialkyl polyglycol ether orthophosphoric ester monoethanolamine salt;

cationic surfactants such as cetyltrimethylammonium chloride.

The following may be mentioned as further adjuvants: viscosity-increasing and emulsion-stabilizing materials such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the abovementioned materials.

Suspensions may be administered orally, dermally or in the form of an injection. They are prepared by suspending the active compound in a liquid excipient, if appropriate with addition of other adjuvants such as wetters, colorants, absorption accelerators, preservatives, antioxidants, UV stabilizers.

Liquid excipients which may be mentioned are all homogeneous solvents and solvent mixtures.

Wetters (dispersants) which may be mentioned are the surfactants indicated further above.

Further adjuvants which may be mentioned are those indicated further above.

Semisolid preparations can be administered orally or dermally. They are distinguished from the above-described suspensions and emulsions only by their higher viscosity.

To prepare solid preparations, the active compound is mixed with suitable excipients, if appropriate using adjuvants, and shaped as desired.

Adjuvants which may be mentioned are all physiologically tolerated solid inert materials. Suitable as such are inorganic and organic materials. Examples of inorganic materials are sodium chloride, carbonates such as calcium carbonate, hydrogen carbonates, aluminium oxides, silicas, clays, precipitated or colloidal silicon dioxide, phosphates.

Examples of organic materials are sugar, cellulose, foods and feedstuffs such as dried milk, animal meals, fine and coarse cereal meals, starches.

Adjuvants are preservatives, antioxidants, colorants which have already been indicated further above.

Other suitable adjuvants are lubricants and glidants such as, for example, magnesium stearate, stearic acid, talc, bentonites, disintegrants such as starch or crosslinked polyvinylpyrrolidone, binders such as, for example, starch, gelatine or linear polyvinylpyrrolidone, and dry binders such as microcrystalline cellulose.

The active compounds may also be present in the compositions as a mixture with synergists or with other active compounds which act against pathogenic endoparasites. Examples of such active compounds are L-2,3,5,6-tetrahydro-6-phenyl-imidazolthiazol, benzimidazol carbamates, praziquantel, pyrantel, febantel, ivermectin.

Ready-to-use preparations comprise the active compound in concentrations of 10 ppm to 20% by weight, preferably 0.1 to 10% by weight Preparations which are diluted prior to use comprise the active compound in concentrations of 0.5 to 90% by weight, preferably 5 to 50% by weight.

In general, it has proved advantageous to administer amounts of approximately 1 to 100 mg of active compound per kg body weight per day, to achieve effective results.

The use of the active compounds according to the invention can be seen from the examples which follow.

EXAMPLE 1

Testing Substances on Infected Neospora Caninum Cell Cultures

The substances were tested in 96-well plates (Falcon 3872). First, a cell culture monolayer of the host cells (Vero or ED) was established on the cell culture plates. To this end, two 50 ml tissue culture flasks (total cell culture area 50 cm$^3$) with an established uninfected monolayer were required for this purpose. The cell lawn of this culture was detached in a $CO_2$-incubator at 37° C. using 5 ml trypsin-EDTA (Gibco, 45300-019). After an incubation time of 10 minutes, most of the cells had become detached. Using a 5 ml pipette, the cell suspension was transferred into a 50 ml centrifuge tube (Greiner, B 769331) by first introducing approximately 1 ml of foetal calf serum which had been warmed slightly. After centrifugation for 5 minutes at 1500 rpm (Varifuge 3.0, Heraeus), the supernatant was discarded, and the cell pellet was resuspended in 100 ml of RPMI medium (95% RPMI 1640, 2% FCS, 1% L-glutamin, 1% sodium bicarbonate, 1% penicillin/streptomycin). 150 µl of this cell suspension were pipetted into each well of a 96-well plate. 100 ml of medium are sufficient for coating 6 microwell plates. Coated cell culture plates were cultured in an incubator at 37° C. for 24 hours under 5% $CO_2$. Then, they were infected with Neospora canicum tachyzoites at a concentration of 48,000 tachyzoites per well followed by a further incubation for 24 hours at 37° C. and 5% $CO_2$. The test substances were weighed into 1.5 ml Eppendorf tubes, the quantity weighed in amounting to 0.5 to 1.5 mg. Then, 1 ml of DMSO was pipetted in per mg of substance, which corresponds to a dilution of $1 \times 10^{-3}$ g/ml. The treatment medium, in which the further dilution series were carried out, consisted of 87% RPMI 1640, 10% FCS, 1% L-glutamin, 1% sodium bicarbonate, 1% penicillin/streptomycin. The concentrations $10^{-5}$, $10^{-6}$ and $10^{-7}$ g/ml were employed for the first screening. 24 hours after infection with Neospora caninum, the diluted preparations were transferred to the cell culture plates in a volume of 150 µl/well. In the first series, untreated medium was used, and this series contained both the infected control and the uninfected control. Then, the cell plates were incubated for 5 days at 37° C. and 5% $CO_2$. Microscopic evaluation was carried out 4 days after the beginning of the treatment and 5 days after the infection under a reverse microscope at 25×10 magnification, using the following key:

| Assessment | Visual appearance |
|---|---|
| 0 = no action | monolayer completely destroyed |
| 1 = weak action | monolayer destroyed to some extent, nests of parasites discernible |
| 2 = full action | monolayer unharmed, no tachyzoites visible |
| T = cytotoxic | cells dead, rounded up |

EXAMPLE 2

In-vitro Results: Table

Test results: *Neospora caninum* in cell culture

| Product | Dose in g/ml | | |
|---|---|---|---|
| | $10^{-5}$ | $10^{-6}$ | $10^{-7}$ |
| Benfluralin | 2 | 2 | 1 |
| Butralin | 2 | 2 | 0 |
| Chlorbufam | T/2 | 0 | — |
| Chlorpropham | T/2 | 2 | 1 |
| Dinitramid | 2 | 2 | 2 |
| Enthalfluralin | 2 | 2 | 1 |
| Isopropalin | T/2 | T/2 | 0 |
| Nitralin | 2 | 2 | 0 |
| Oryzalin | T | 2 | 1 |
| Profluralin | 2 | 2 | 0 |
| Propham | T/2 | 2 | 1 |
| Trifluralin | T/2 | 2 | 1 |

The abbreviations used in the example have the following meanings:

$CO_2$=carbon dioxide
DMSO=dimethyl sulphoxide
ED=equine dermal cell line
EDTA=ethylenediaminetetraacetic acid
FCS=foetal calf serum
RPMI=growth medium for cell cultures
rpm=rotations per minute
VERO=African green monkey kidney cell line

What is claimed is:

1. A method for controlling diseases in an animal infected by at least one protozoan of the genus Neospora, comprising the step of administering to said animal an amount of a plant microtubulin inhibitor in a therapeutically effective amount sufficient to control said diseases.

* * * * *